United States Patent [19]

Freedman et al.

[11] Patent Number: 5,404,883
[45] Date of Patent: Apr. 11, 1995

[54] GRAY SCALE WINDOWING

[75] Inventors: Zvi Freedman, Kiryat Bialik; Naftali Goldberg; Elan Lifshitz, both of Haifa; Jacob Reshef, Kiryat Motzkin, all of Israel

[73] Assignee: Elscint Ltd., Haifa, Israel

[21] Appl. No.: 295,039

[22] Filed: Aug. 25, 1994

Related U.S. Application Data

[63] Continuation of Ser. No. 74,559, Jun. 11, 1993, abandoned.

[30] Foreign Application Priority Data

Jun. 25, 1992 [IL] Israel ..................................... 102314

[51] Int. Cl.6 .............................................. A61B 8/00
[52] U.S. Cl. .............................................. 128/660.07
[58] Field of Search ....................... 128/660.01, 660.07, 128/661.01; 364/413.13, 413.25; 73/602, 603, 606; 356/5; 358/160

[56] References Cited

U.S. PATENT DOCUMENTS

| | | | |
|---|---|---|---|
| 4,052,889 | 10/1977 | Mucciardi et al. | 73/602 |
| 4,417,276 | 11/1983 | Bennett et al. | 358/160 |
| 4,960,329 | 10/1990 | Schofield | 356/5 |
| 5,079,698 | 1/1992 | Grenier et al. | 364/413.13 |
| 5,268,876 | 12/1993 | Rachlin | 128/661.01 |

Primary Examiner—George Manuel
Attorney, Agent, or Firm—Sandler, Greenblum & Bernstein

[57] ABSTRACT

An automatic windowing system for ultrasonic imaging wherein the incoming signal is separated into a high spatial frequency component and a low spatial frequency component. A comparatively low ratio of compression is applied to the high spatial frequency component while a high ratio of compression is applied to the low spatial frequency component. The two components after compression are added to form the signal used for display.

7 Claims, 1 Drawing Sheet

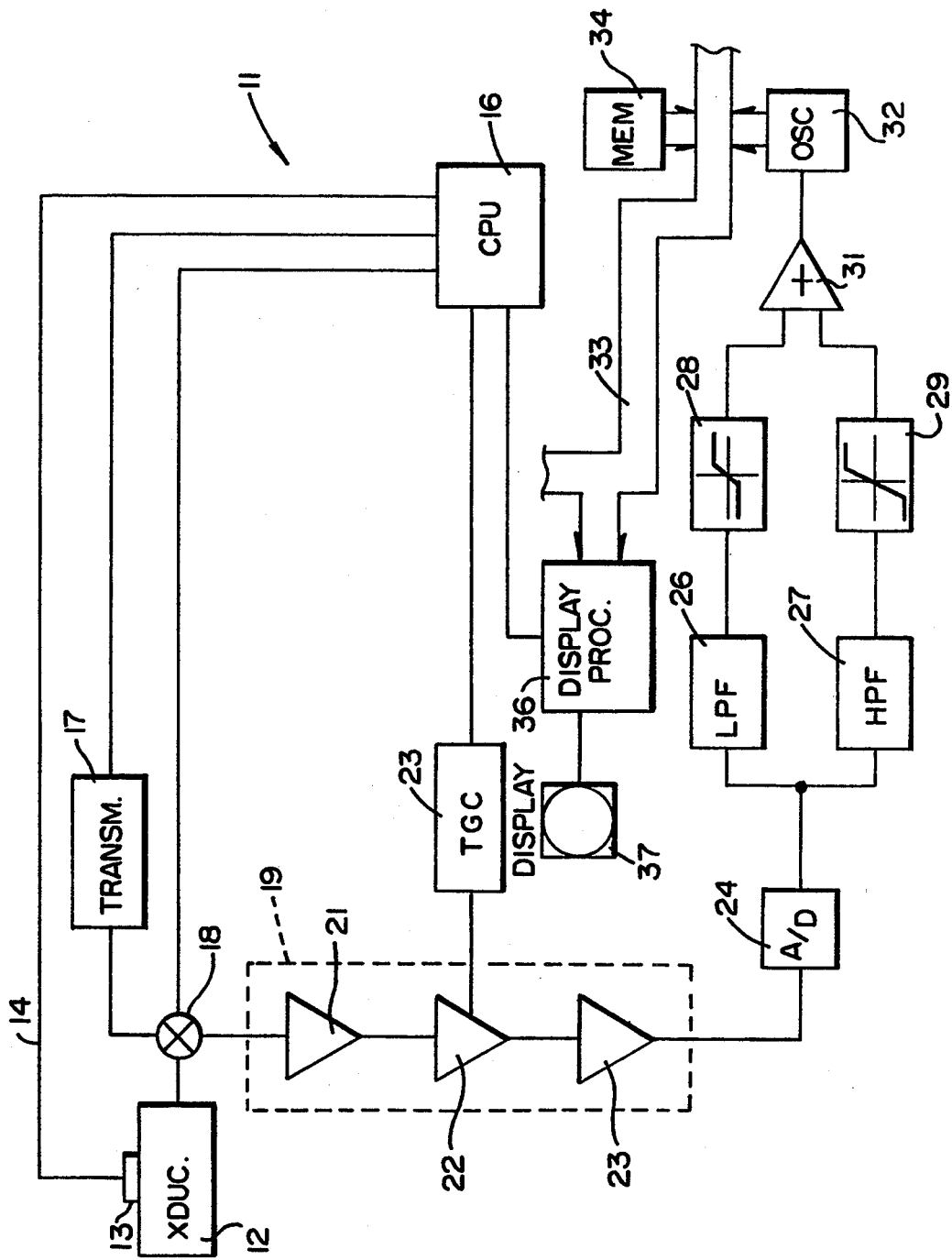

GRAY SCALE WINDOWING

This application is a continuation, of application Ser. No. 08/074,559, filed Jun. 11, 1993, now abandoned.

FIELD OF THE INVENTION

This invention is concerned with ultrasonic scanning systems for medical diagnostic imaging and more particularly with gray scale windowing for such systems and for other diagnostic imaging systems.

BACKGROUND OF THE INVENTION

Medical diagnostic imaging systems in general acquire signals from the interior of a patient's body. To generate the image, the location of the source and the relative intensity of each of the signals must be determined. The intensities of the signals are measured and converted into gray scales.

For example, ultrasonic scanning systems acquire data to provide medical images of the interior of patients. In general, the systems use transducers to transmit ultrasonic waves in the order of several Mhz. in frequency into a subject or a patient. "Echo" signals are received responsive to these transmitted ultrasonic waves and are used as data for the images. The transducers are positioned juxtaposed to the patient's body. The intensities of the received echo signals are measured and converted into gray scale determinations ranging from white to black. The location of source, that is the echo generating material (i.e., boundaries of organs and the like) is basically determined by the time required for the echo to return after the original signal is transmitted. The acquisition of the intensity data correlated to location in the body of the source of the signal enables obtaining intensity values for image pixels which correspond to body locations as is well known when providing images.

As the transmitted waves travel through the body they are attenuated. The received echo signals are relatively weak and require amplification. In practice, the gain of the amplification is varied by time gain compensation (TGC) circuitry which overcomes the attenuation of the echo signal caused by the distance the origin of the echo signal is from the transducer.

The intensities of the echo signals in medical imaging systems are characterized by dynamic range; i.e., a gray range greatly exceeding display capabilities. The echo intensities depend upon such things as:

1. intensity of the target or source; i.e., the transmitted signal at the point from which the echo signal emanates;
2. the target impedance mismatch to surroundings;
3. the target's geometrical orientation; and
4. attenuation of the acoustic signal by the tissue.

Diagnostic pulse echo systems using ultrasound for examination of targets deep within the body will typically produce echo signals spanning a dynamic intensity amplitude range of 100 dB or more. In any given range segment, target acoustic impedance differences from the surroundings and geometrical orientation will provide variations in echo strength of 30–50 dB. This represents the desired target information. The additional 50–70 dB variations originating from the tissue attenuation over the total path length represents an unwanted component. These additional 50–70 dB variations are taken care of by the TGC circuitry which compensates for intensity variations of the echo due to absorption.

Direct observation of signals in the 30–50 dB dynamic range is not practical with conventional display devices. Therefore, it is apparent that it is not practical to enable viewing more than a small segment of the entire dynamic range at any one time.

Thus, ultrasound systems generate images by converting echoes of different amplitudes into image points of different brightness. The brightness is expressed by a graduated gray scale where lower amplitude echoes are resolved as darker shades of gray and higher amplitude echoes as brighter shades. The assignment of a given gray shade to a particular echo amplitude is arbitrary and it is determined by an echo to gray shade conversion curve employed during processing of the data. In fact, there are over 1,000 shades of gray in ultrasound images after the TGC. The present state of the art ultrasound systems reduce this 1,000 shades of gray by methods such as logrithmically compressing the data; i.e., a variable gain is used as a function of the signal level. The higher the signal level, the lower the gain. Thus, for example, the differential gains at high input levels may be only about 0.01 of the gain at the lower signal input levels.

Therefore, when logrithmic data compression systems are used, clinical information that may be expressed as small local variations of high signal input levels are lost.

Another prior art solution to the problem of adapting the 1,000 shades of gray to what is presently available with regard to TV monitors and the limits of human vision; i.e., approximately 100 shades of gray, is off-line windowing. In using such windowing, the operator manually selects the optimal signal input level range to be displayed as the full range of the monitor. This method is faulty for ultrasound because:

1. the optimum window is local in nature thereby optimizing the image at a certain region will generally result in causing a deterioration of the image at other regions; and
2. the method is difficult to implement on line.

BRIEF DESCRIPTION OF THE PRESENT INVENTION

In accordance with a preferred embodiment of the present invention, an automatic windowing system is provided wherein the windowing is accomplished as a function of spatial frequency; i.e., the incoming signal is processed after TGC to separate it into two components, a high spatial frequency component and a low spatial frequency component. Then a comparative low ratio compression is used with the high spatial frequency component while a high ratio of compression is used in compressing the low spatial frequency component. The two components are then added together to form the signal that is processed for display purposes.

More particularly, an automatic windowing method for ultrasound imaging systems is provided in order to maximize the utilization of variations in detector signal intensity, said method comprises the steps of:

transmitting ultrasonic signals into a subject,
receiving echo signals responsive to the transmitted ultrasonic signals,
separating the echo signals into a first spatial frequency signal and a second spatial frequency signal, compressing the amplitudes of the first spatial frequency intensity signals in a first compressor,
compressing the amplitudes of the second spatial frequency intensity signals in a second compressor with a higher compression ratio than the compression of the first spatial frequency signals; thereby, compressing the second spatial frequency signals more than the first spatial frequency signals are compressed, combining the outputs of the two compressors, and processing the combined signals for providing a display of the image.

In a preferred embodiment, the first spatial frequency signal are high frequency signals. The result is that all minor details which may exist as small high spatial frequency changes of the otherwise high spatial frequencies are retained. This method obviates some of the disadvantages of prior art systems.

BRIEF DESCRIPTION OF THE DRAWING

The above mentioned and other features and objects of the present invention will be better understood when considered in the light of the following description taken in conjunction with the accompanying drawing showing a block diagram of the inventive system.

GENERAL DESCRIPTION

The ultrasonic system 11 of the FIGURE includes the transducer 12 which may be of the type that is held against a patient's body and automatically scans a prescribed sector area by transmitting ultrasonic signals into the body. A monitor 13 is preferably provided for monitoring the direction of the beam emitted by the transducer. The monitor 13 is shown as being connected by line 14 to a central processing unit 16 that controls the output timing and operation of the various units of the ultrasonic imaging system 11.

The transducer 12 has two modes: a transmitting mode and receiving mode. When it is in the transmitting mode, then a transmitter 17 applies ultrasonic pulse signals through a switching means 18 to the transducer 12 to cause the transducer to transmit an ultrasonic pulse wave into the subject. In the receiving mode, the switch 18 connects the transducer 12 to a receiver 19. The transducer 12 detects echoes coming back from the interior of the subject's body.

The ultrasonic pulsed waves are generated when a high voltage pulse is applied, for example, to a piezoelectric crystal. The crystal generates a short burst of ultrasonic energy in response to this excitation. The ultrasonic wave undergoes attenuation as it travels through biological material due to scattering and absorption.

The transducer is preferably acoustically coupled to the patient by a thin layer of mineral oil on the skin. The ultrasonic pulse travels through patient in a relatively well defined beam. The velocity of the ultrasound through soft tissues of the body ranges from about 1,459 mm per sec. to about 1,610 mm per sec.; with an average of 1,550 mm per sec. During its propagation, the ultrasonic pulse encounters interfaces between different tissue structures. A portion of the ultrasonic energy which portion depends on the degree of mismatch between tissues, is reflected as an echo.

Since tissues in general have similar acoustic impedances, only a small percentage of the incident energy is reflected at each interface so that the ultrasonic beam is capable of penetrating deeper into the body. Since the received echo is relatively small, it is first preamplified in preamplifier 21. The output of the preamplifier 21 is then fed into a variable gain amplifier 22 which is controlled by a TGC circuit 23. The purpose of the TGC circuit in conjunction with the variable gain amplifier is to compensate for the attenuation of the signal as it travels through tissue to the point where the echo rebounds. The output of the variable gain amplifier is then amplified in a processor amplifier 23. The output of the processing amplifier is then converted in analog-to-digital (A/D) converter 24 to a digital form. Within the scope of the invention, of course, the analog form may be maintained. However, it is preferable to utilize the A/D circuit 24.

The digital output of the A/D circuit is then filtered in both a low pass spatial frequency filter 26 and in parallel in a high pass spatial frequency filter 27. The output of the low pass filter 26 is a low spatial frequency signal. The output of the high pass filter is a high spatial frequency signal.

Thus, the received echo signal originating at the transducer is split into parts: a high frequency signal and a low frequency signal. Each of these two signals are then compressed by two different compressors, such as compressor 28 and compressor 29. Compressor 28 is shown as having a high compression ratio. The signal out of the low pass filter; i.e., the low frequency signal is compressed at the high compression ratio of the compressor 28. On the other hand, the high frequency signal of filter 27 is compressed in a compressor 29 which has a much lower compression ratio. The lower compression ratio of the high frequency signal enables maintaining the small high frequency variations at the output of the compressor. The output of the two compressors 28 and 29 are summed together in summation circuit 31. The output of the summation circuit 31 is applied to a digital scan converter (DSC) circuit, which preprocesses the data for display purposes. The output of the DSC circuit 32 goes to a high speed bus 33. Connected to the high speed bus is a memory 34 and a display processor 36. The display processor works in conjunction with the memory 34 to construct a pixel-by-pixel image for display on display unit 37.

Note that the central processing unit controls the operation of the system components such as the DSC circuit 32, the display processor 36, the TGC circuit 23, the transmission circuit 17, the switch 18 and the monitoring of the direction of the transducer 12.

In operation, an automatic windowing system is provided for ultrasound imaging systems. The automatic windowing system uses the spatial frequency of the signals to divide the signal into two parts: a high spatial frequency signal and a low spatial frequency signal. The low spatial frequency signal is subjected to a high compression ratio, such as, for example, a compression ratio of 10:1 and the high spatial frequency signal is subjected to a much lower compression, such as a compression ratio of 2:1. The signals which are, in fact, automatically windowed by the compression ratios applied to the output of the low pass filter and the output of the high pass filter are then combined in summation circuit 31.

The combined signals are used by the DSC circuit and the display processor to provide an improved displayed image.

While the invention has been explained using a particular embodiment, it should be understood that this embodiment is described merely by way of example, and not as a limitation on the scope of the invention.

What is claimed is:

1. An automatic windowing method for ultrasound imaging systems for maximizing the utilization of variations in detected signal intensity, said method comprising the steps of:

determining the spatial frequency intensity of the detected signals, and compressing the determined spatial frequency intensity of said detected signals, windowing as a function of said compressed determined spatial frequency of said detected signals for maximizing variations in ultrasound images.

2. An automatic windowing method for ultrasound imaging systems to maximize utilization of variations in detected signal intensity, said method comprising the steps of:

transmitting ultrasonic signals into a subject, receiving echo signals responsive to the transmitted ultrasonic signals, dividing the echo signals into high spatial frequency intensity signals and low spatial frequency intensity signals.

compressing the high spatial frequency signals in a first compressor for decreasing the range of the intensities of the high spatial frequency signals, compressing the low spatial frequency signals for decreasing the range of the intensities of the low spatial frequency signals with a different compression ratio than used for compressing the high spatial frequency signals, combining the compressed low spatial frequency signals and the compressed high spatial frequency signals, and processing the combined signals for providing display images optimizing the use of the intensities of the detected signals.

3. An automatic windowing method for ultrasound imaging systems to maximize utilization of variations in detected signal intensity, said method comprising the steps of:

transmitting ultrasonic signals into a subject, receiving echo signals responsive to the transmitted ultrasonic signals, dividing the echo signals into high spatial frequency intensity signals and low spatial frequency intensity signals, compressing the high spatial frequency intensity signals in a first compressor for decreasing the range of the intensities of the high spatial frequency signals, compressing the low spatial frequency signals in a second compressor for decreasing the range of the intensities of the low spatial frequency signals with a higher compression ratio than used for compressing the high spatial frequency signals, combining the outputs of the first and second compressors, and processing the combined signals for providing a display image optimizing the use of the intensities of the detected signals.

4. The automatic windowing method of claim 3 wherein the step of dividing the echo signals into a high spatial frequency intensity signal and a low spatial frequency intensity signal comprises filtering to obtain a pass band of low spatial frequency signals, and a pass band of high spatial frequency signals.

5. An automatic windowing system for diagnostic ultrasonic imaging systems to maximize utilization of variations in detected signal intensity, said system comprising:

a transmitter for transmitting ultrasonic signals into a patient, said transmitter utilizing an ultrasound transducer, a receiver for receiving echo signals obtained responsive to the transmitted ultrasonic signals, said receiver also utilizing said ultrasonic transducer, a filter for filtering the received signals into high spatial frequency intensity signals and low spatial frequency intensity signals, a first signal compressor for decreasing the intensity range of the high spatial frequency intensity signals, a second signal compressor for decreasing the intensity range of the low spatial frequency intensity signals with a different compression ratio than used for compressing the high spatial frequency signals, a combiner for combining the outputs of the two compressors, and a processor for processing the combined signals to provide a display image optimizing the use of the intensities of the detected signals.

6. The automatic windowing apparatus of claim 5 wherein said filter comprises a first filter for providing a low spatial frequency pass band and a second filter for providing a high spatial frequency pass band.

7. The automatic windowing apparatus of claim 5 wherein the combiner comprises a summing circuit.

* * * * *